(12) United States Patent
Ehringer et al.

(10) Patent No.: US 8,187,837 B2
(45) Date of Patent: May 29, 2012

(54) OPTIMIZED PURIFICATION PROCESS OF RECOMBINANT GROWTH FACTOR PROTEIN

(75) Inventors: Ute Ehringer, Waghäusel (DE); Eva Kohlstrung, Plankstadt (DE)

(73) Assignee: Biopharm Gesellschaft zur biotechnologischen Entwicklung von Pharmaka mbH, Heidelberg (DE)

( * ) Notice: Subject to any disclaimer, the term of this patent is extended or adjusted under 35 U.S.C. 154(b) by 73 days.

(21) Appl. No.: 12/670,734

(22) PCT Filed: Jun. 20, 2008

(86) PCT No.: PCT/EP2008/005016
§ 371 (c)(1),
(2), (4) Date: Jul. 15, 2010

(87) PCT Pub. No.: WO2009/015736
PCT Pub. Date: Feb. 5, 2009

(65) Prior Publication Data
US 2011/0160441 A1    Jun. 30, 2011

(30) Foreign Application Priority Data

Jul. 27, 2007    (EP) .................................... 07014798

(51) Int. Cl.
*C12P 21/00*    (2006.01)
*C12N 1/06*    (2006.01)
*C12N 1/21*    (2006.01)
*C07K 14/51*    (2006.01)

(52) U.S. Cl. .................. 435/69.1; 435/259; 435/252.33; 562/560; 530/350

(58) Field of Classification Search ........................ None
See application file for complete search history.

(56) References Cited

U.S. PATENT DOCUMENTS

| 5,658,882 | A | 8/1997 | Celeste |
| 5,804,416 | A | 9/1998 | Wolfman |
| 5,866,364 | A | 2/1999 | Israel |

FOREIGN PATENT DOCUMENTS

| EP | 1 273 655 | * | 1/2003 |
| EP | 1 439 190 | * | 7/2004 |
| EP | 1 449 848 | * | 8/2004 |
| EP | 1 698 691 A1 | * | 9/2006 |
| WO | WO 99/61611 | * | 12/1999 |
| WO | WO 00/20591 | * | 4/2000 |

OTHER PUBLICATIONS

Seemann et al. Activating and deactivating mutations in the receptor interaction site of GDF5 cause symphalangism or brachydactyly type A2. J Clin Invest. Sep. 2005;115(9):2373-81. Epub Aug. 25, 2005.*

* cited by examiner

*Primary Examiner* — David Romeo
(74) *Attorney, Agent, or Firm* — Rothwell, Figg, Ernst & Manbeck, P.C.

(57) ABSTRACT

A process for the production of a purified recombinant GDF-5 related protein in prokaryotes comprises the steps of bacterial cell disruption and inclusion body solubilization to obtain a solubilized monomer of a GDF-5 related protein, said process characterized by a) disruption of bacterial cells with a high pressure homogenizer at a disruption pressure between 800 and 900 bar; and/or b) treatment of the recovered inclusion bodies with a denaturing solubilization buffer comprising L-arginine.

10 Claims, 10 Drawing Sheets

```
        1   MRLPKLLTFL  LWYLAWLDLE  FICTVLGAPD  LGQRPQGTRP  GLAKAEAKER
PPLARNVFRP
       61   GGHSYGGGAT  NANARAKGGT  GQTGGLTQPK  KDEPKKLPPR  PGGPEPKPGH
PPQTRQATAR
      121   TVTPKGQLPG  GKAPPKAGSV  PSSFLLKKAR  EPGPPREPKE  PFRPPPITPH
EYMLSLYRTL
      181   SDADRKGGNS  SVKLEAGLAN  TITSFIDKGQ  DDRGPVVRKQ  RYVFDISALE
KDGLLGAELR
      241   ILRKKPSDTA  KPAAPGGGRA  AQLKLSSCPS  GRQPASLLDV  RSVPGLDGSG
WEVFDIWKLF
      301   RNFKNSAQLC  LELEAWERGR  AVDLRGLGFD  RAARQVHEKA  LFLVFGRTKK
RDLFFNEIKA
      361   RSGQDDKTVY  EYLFSQRRKR  RAPLATRQGK  RPSKNLKARC  SRKALHVNFK
DMGWDDWIIA
      421   PLEYEAFHCE  GLCEFPLRSH  LEPTNHAVIQ  TLMNSMDPES  TPPTCCVPTR
LSPISILFID
      481   SANNVVYKQY  EDMVVESCGC  R
```

FIG. 1    Human GDF-5 Precursor Protein

```
hGDF-6 : CSKRPLHVNFRELGWDDWIIAPLEYEAYHCEGVCDFPIRSHLEPTNHAIIQTLMNSMDEGSTEPSCCVETKLTPISILYIDAGNVVV : 87
hGDF-7 : CSRRPLHVDFKELGWDDWIIAPLDYEAYHCEGLCDFPIRSHLEPTNHAIIQTLLNSMAEDAAPASCCVPARLSPISILYIDAANVVV : 87
hGDF-5 : CSRRALHVNFKDMGWDDWIIAPLEYEAFHCEGLCEFPIRSHLEPTNHAVIQTLMNSMDEESTEPTCCVETRLSPISILFILSANVVV : 87 hGDF-6 : YKQYEDMVVESCGCR
hGDF-7 : YKQYEDMVVEACGCR
hGDF-5 : YKQYEDMVVESCGCR
```

FIG. 2         Sequence Comparison GDF-5/GDF-6/GDF-7 (Cys-Knot)

% sequence identity to
cystine-knot-domain of human GDF-5

| Sequence | % Identity | Identical Residues |
|---|---|---|
| GDF-5 Homo | 100 | 102/102 |
| GDF-5 Mus | 99 | 101/102 |
| GDF-6 Mus | 86 | 88/102 |
| GDF-6 Homo | 85 | 87/102 |
| GDF-6 Xenopus | 84 | 86/102 |
| GDF-6 Bos | 83 | 85/102 |
| GDF-7 Homo | 81 | 83/102 |
| GDF-7 Macaca | 80 | 82/102 |
| GDF-7 Mus | 80 | 82/102 |
| BMP-4 | 57 | 58/102 |
| Vg-1 | 52 | 53/102 |
| DPP | 52 | 53/102 |
| BMP-5 | 52 | 53/102 |
| BMP-9 | 51 | 52/102 |
| BMP-10 | 51 | 52/102 |
| BMP-8A | 51 | 51/102 |
| BMP-6 | 51 | 52/102 |
| BMP-7 | 51 | 52/102 |
| GDF-3 | 49 | 50/102 |
| 60A | 48 | 49/102 |
| BMP-8B | 48 | 49/102 |
| BMP-3A | 47 | 48/103 |
| GDF-9B | 45 | 46/102 |
| BMP-3B | 43 | 44/103 |
| GDF-8 | 37 | 38/102 |
| GDF-12 | 37 | 38/104 |
| GDF-11 | 36 | 37/102 |
| GDF-9 | 32 | 33/102 |

FIG. 3         Sequence Comparison of different Cys-Knot Proteins

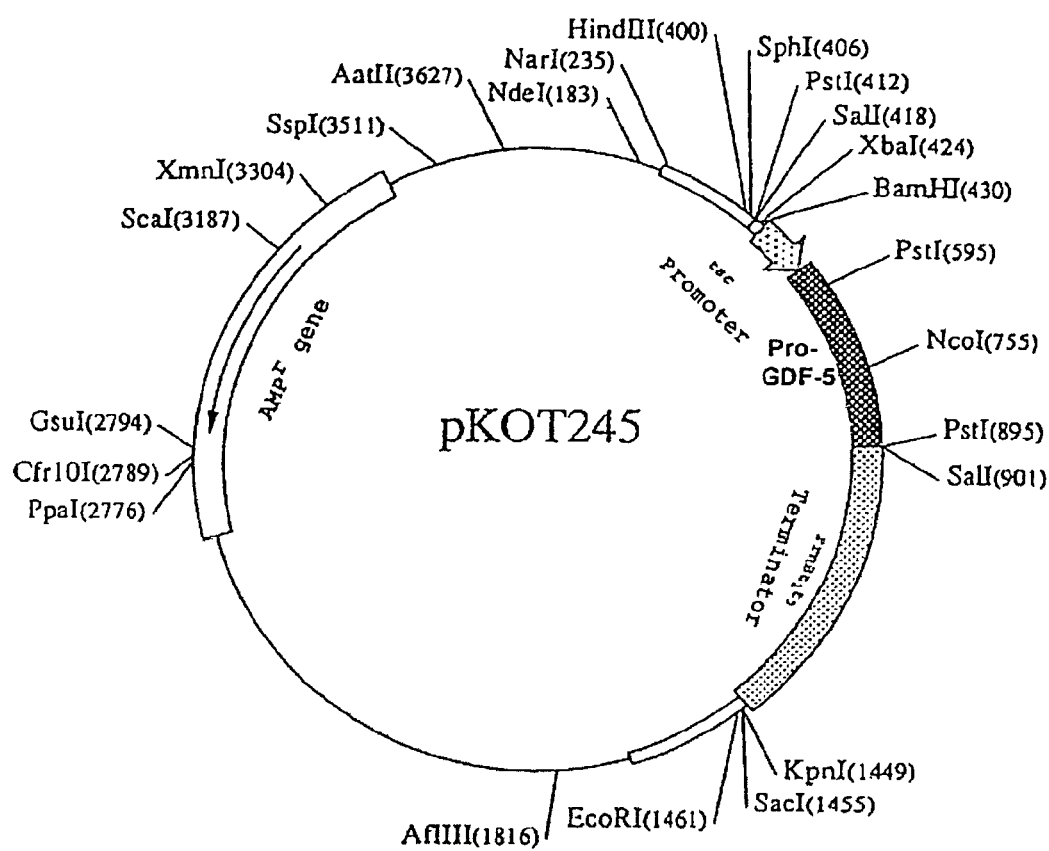
FIG. 4    GDF-5 Expression Vector

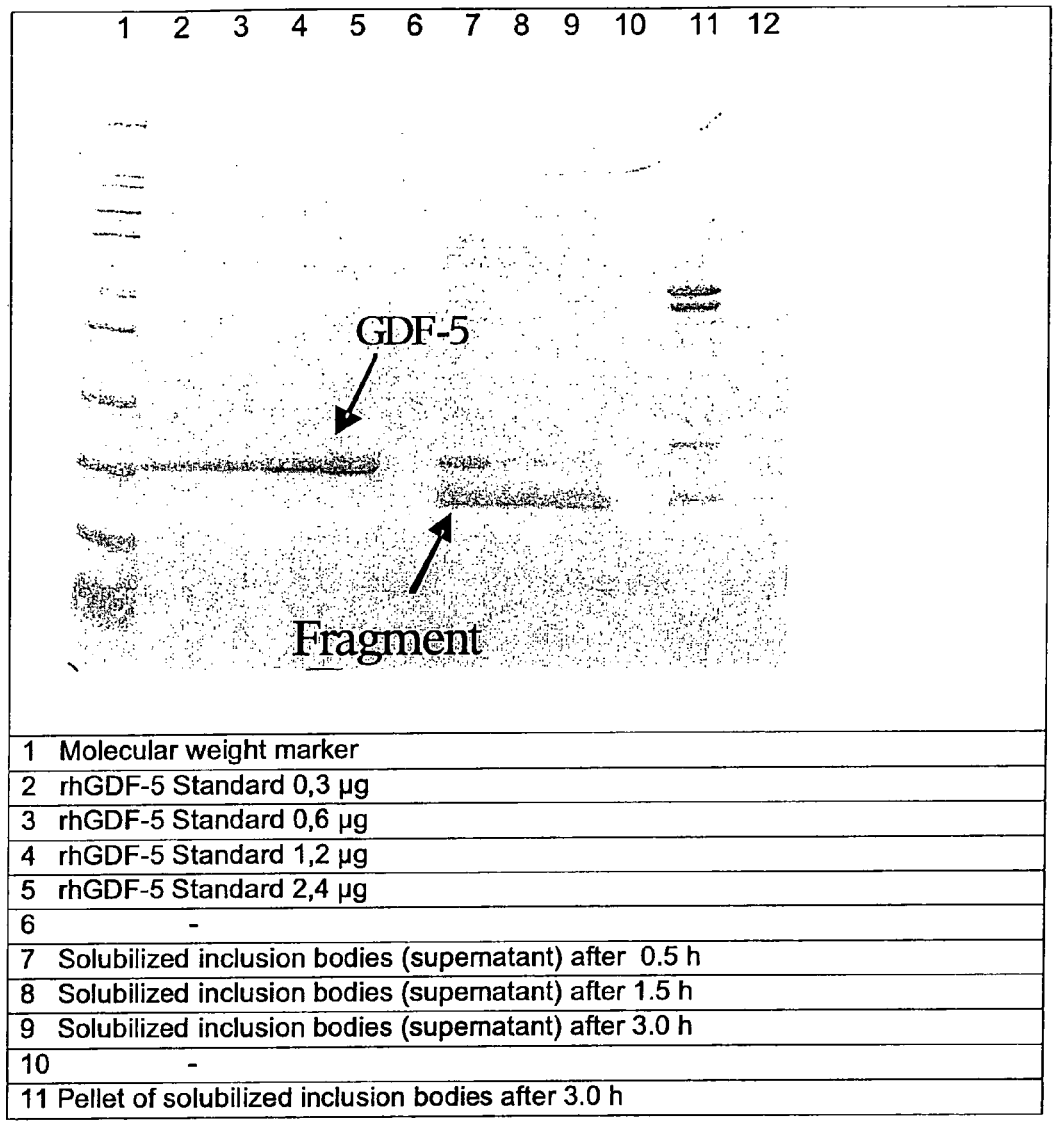
FIG. 5  Fragmentation of GDF-5 in Standard Solubilization Buffer

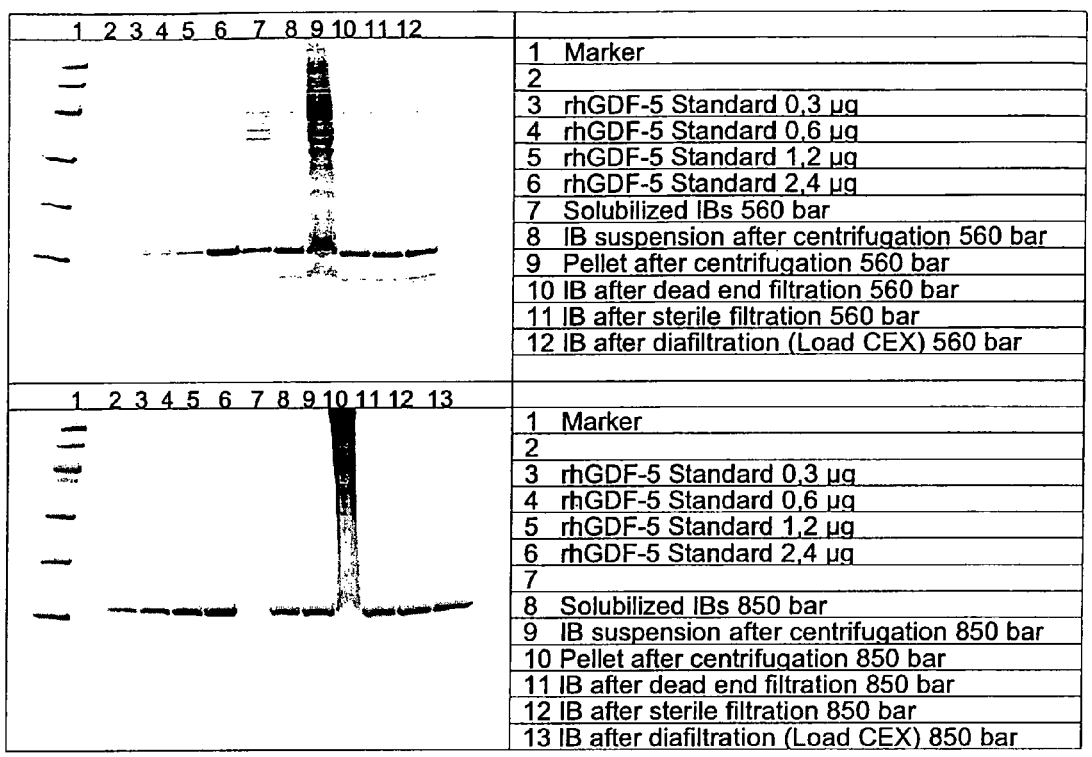
FIG. 6 Effect of Disruption Pressure on Fragmentation/Yield/Purity

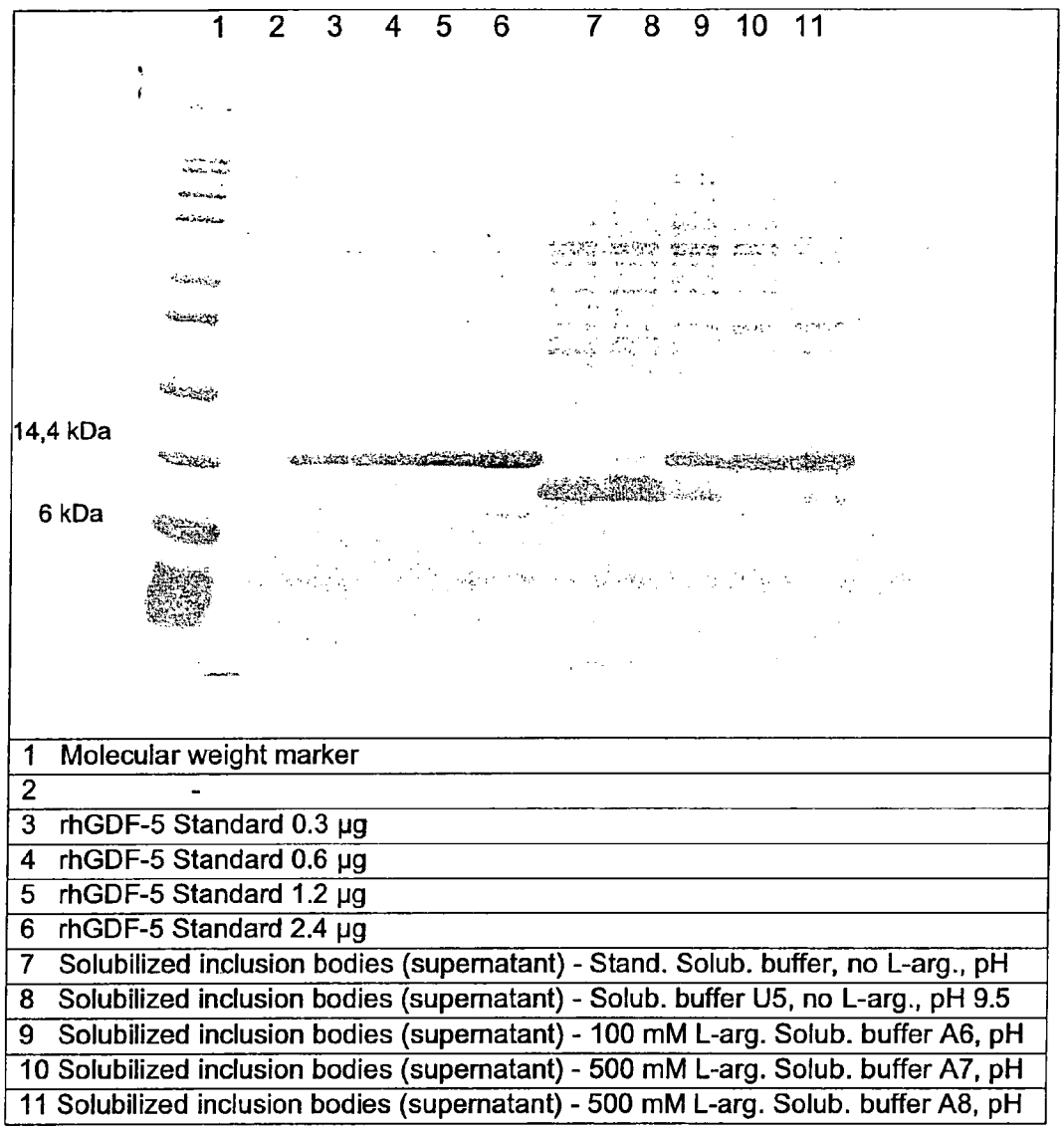
FIG. 7  Effect of L-arginine, pH on Protein Degradation (4 h incubation)

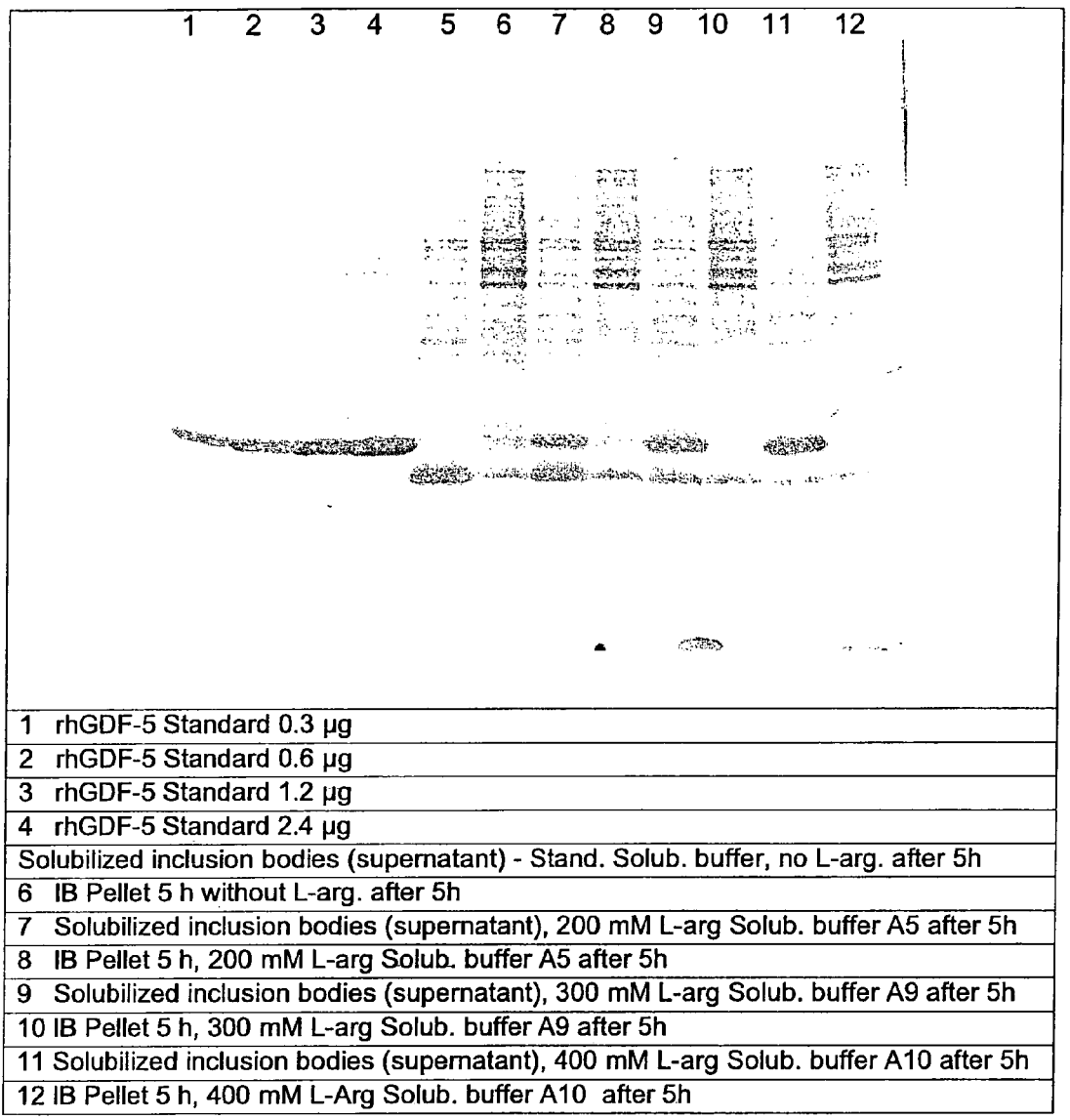
FIG. 8　Effect of L-arginine, pH on Protein Degradation

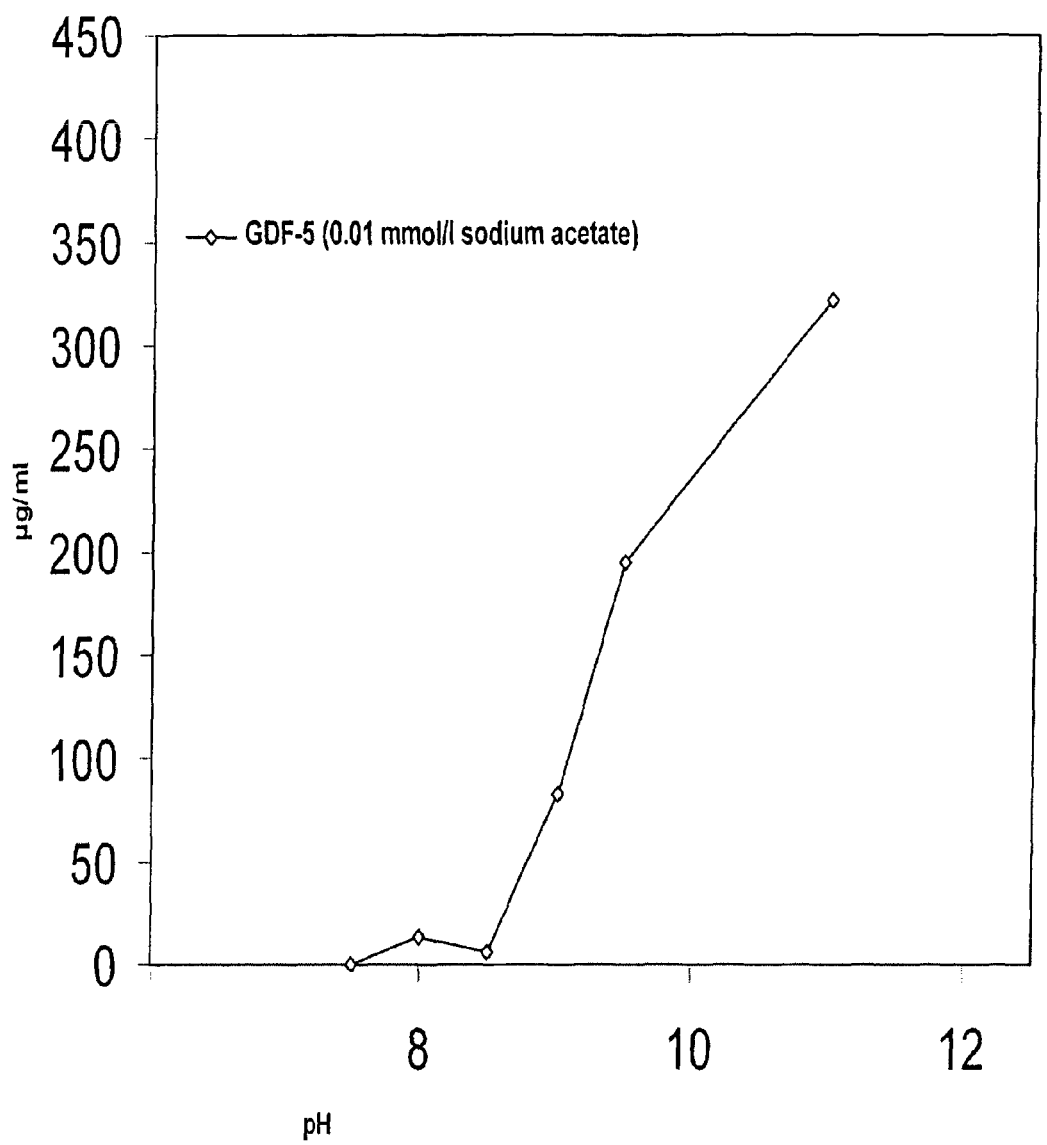
FIG.9   GDF-5 Solubility Profile

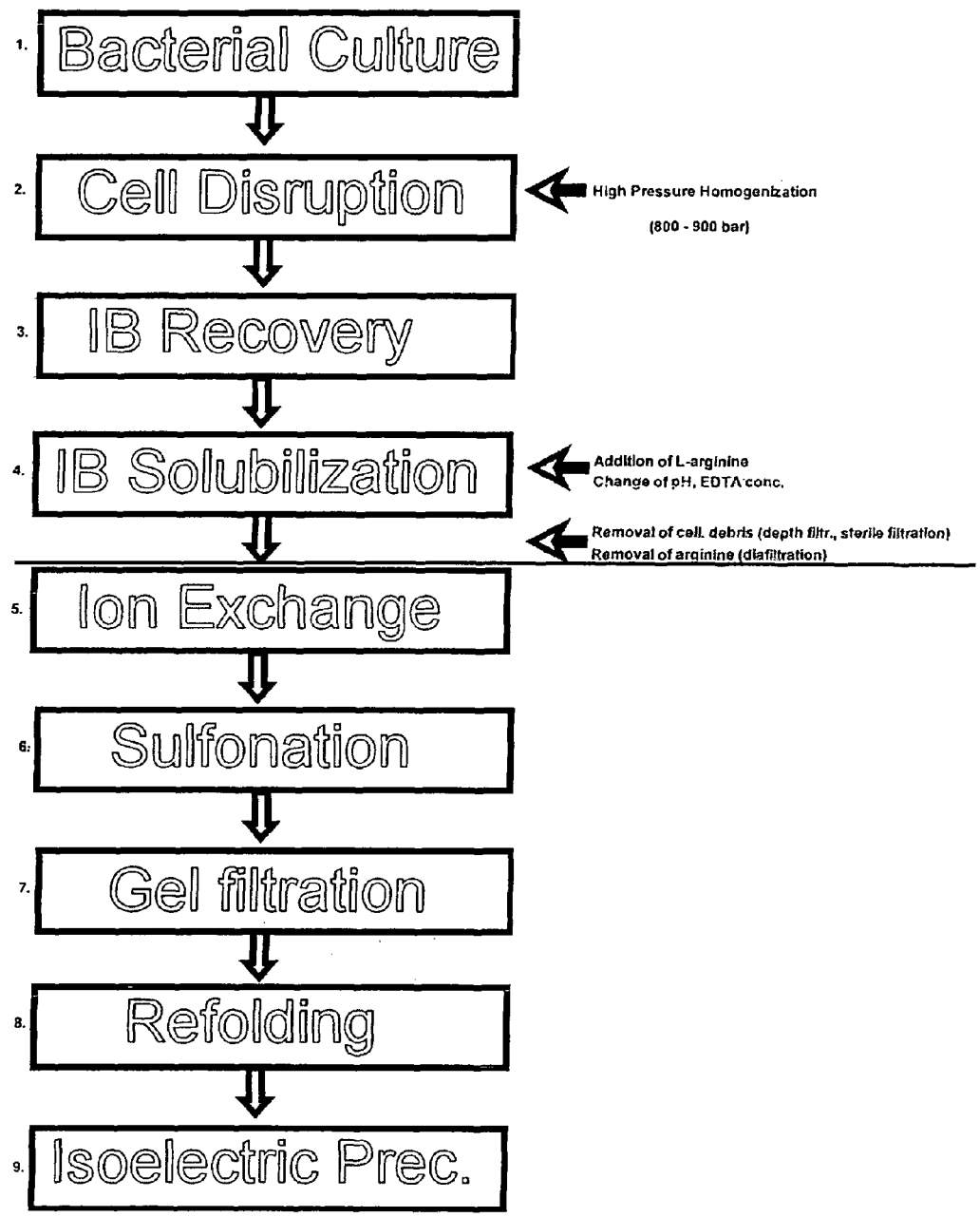
FIG. 10  Proposed modifications of the GDF-5 purification process

```
                        SEQUENCE LISTING

<160> NUMBER OF SEQ ID NOS: 7

<210> SEQ ID NO 1
<211> LENGTH: 501
<212> TYPE: PRT
<213> ORGANISM: Homo sapiens
<220> FEATURE:
<221> NAME/KEY: MISC_FEATURE
<222> LOCATION: (1)..(501)
<223> OTHER INFORMATION: GDF-5 precursor

<400> SEQUENCE: 1

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
            20                  25                  30

Gln Arg Pro Gln Gly Thr Arg Pro Gly Leu Ala Lys Ala Glu Ala Lys
        35                  40                  45

Glu Arg Pro Pro Leu Ala Arg Asn Val Phe Arg Pro Gly Gly His Ser
    50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125

Pro Gly Gly Lys Ala Pro Pro Lys Ala Gly Ser Val Pro Ser Ser Phe
    130                 135                 140

Leu Leu Lys Lys Ala Arg Glu Pro Gly Pro Pro Arg Glu Pro Lys Glu
145                 150                 155                 160

Pro Phe Arg Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
        195                 200                 205

Gly Gln Asp Asp Arg Gly Pro Val Val Arg Lys Gln Arg Tyr Val Phe
    210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                245                 250                 255

Gly Gly Arg Ala Ala Gln Leu Lys Leu Ser Ser Cys Pro Ser Gly Arg
            260                 265                 270

Gln Pro Ala Ser Leu Leu Asp Val Arg Ser Val Pro Gly Leu Asp Gly
        275                 280                 285

Ser Gly Trp Glu Val Phe Asp Ile Trp Lys Leu Phe Arg Asn Phe Lys
    290                 295                 300

Asn Ser Ala Gln Leu Cys Leu Glu Leu Glu Ala Trp Glu Arg Gly Arg
305                 310                 315                 320
```

-continued

```
Ala Val Asp Leu Arg Gly Leu Gly Phe Asp Arg Ala Ala Arg Gln Val
            325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
            355                 360                 365

Val Tyr Glu Tyr Leu Phe Ser Gln Arg Arg Lys Arg Arg Ala Pro Leu
    370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
                420                 425                 430

Cys Glu Phe Pro Leu Arg Ser His Leu Glu Pro Thr Asn His Ala Val
            435                 440                 445

Ile Gln Thr Leu Met Asn Ser Met Asp Pro Glu Ser Thr Pro Pro Thr
            450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500

<210> SEQ ID NO 2
<211> LENGTH: 2703
<212> TYPE: DNA
<213> ORGANISM: Homo sapiens
<220> FEATURE:
<221> NAME/KEY: CDS
<222> LOCATION: (640)..(2142)

<400> SEQUENCE: 2
ccatggcctc gaaagggcag cggtgatttt tttcacataa atatatcgca cttaaatgag      60
tttagacagc atgacatcag agagtaatta aattggtttg ggttggaatt ccgtttccaa     120
ttcctgagtt caggtttgta aaagattttt ctgagcacct gcaggcctgt gagtgtgtgt     180
gtgtgtgtgt gtgtgtgtgt gtgtgtgtga agtattttca ctggaaagga ttcaaaacta     240
gggggaaaaa aaaactggag cacacaggca gcattacgcc attcttcctt cttggaaaaa     300
tccctcagcc ttatacaagc ctccttcaag ccctcagtca gttgtgcagg agaaaggggg     360
cggttggctt tctcctttca agaacgagtt attttcagct gctgactgga gacggtgcac     420
gtctggatac gagagcattt ccactatggg actggataca aacacacacc cggcagactt     480
caagagtctc agactgagga gaaagccttt ccttctgctg ctactgctgc tgccgctgct     540
tttgaaagtc cactcctttc atggtttttc ctgccaaacc agaggcacct tgctgctgc      600 cgctgttctc tttggtgtca ttcagcggct ggccagagg atg aga ctc ccc aaa       654
                                          Met Arg Leu Pro Lys
                                            1               5 ctc ctc act ttc ttg ctt tgg tac ctg gct tgg ctg gac ctg gaa ttc       702
Leu Leu Thr Phe Leu Leu Trp Tyr Leu Ala Trp Leu Asp Leu Glu Phe
             10                  15                  20 atc tgc act gtg ttg ggt gcc cct gac ttg ggc cag aga ccc cag ggg       750
Ile Cys Thr Val Leu Gly Ala Pro Asp Leu Gly Gln Arg Pro Gln Gly
         25                  30                  35
```

| | | |
|---|---|---|
| acc agg cca gga ttg gcc aaa gca gag gcc aag gag agg ccc ccc ctg<br>Thr Arg Pro Gly Leu Ala Lys Ala Glu Ala Lys Glu Arg Pro Pro Leu<br>    40                      45                    50 | | 798 |
| gcc cgg aac gtc ttc agg cca ggg ggt cac agc tat ggt ggg ggg gcc<br>Ala Arg Asn Val Phe Arg Pro Gly Gly His Ser Tyr Gly Gly Gly Ala<br> 55                      60                    65 | | 846 |
| acc aat gcc aat gcc agg gca aag gga ggc acc ggg cag aca gga ggc<br>Thr Asn Ala Asn Ala Arg Ala Lys Gly Gly Thr Gly Gln Thr Gly Gly<br>70                      75                    80                    85 | | 894 |
| ctg aca cag ccc aag aag gat gaa ccc aaa aag ctg ccc ccc aga ccg<br>Leu Thr Gln Pro Lys Lys Asp Glu Pro Lys Lys Leu Pro Pro Arg Pro<br>                      90                    95                    100 | | 942 |
| ggc ggc cct gaa ccc aag cca gga cac cct ccc caa aca agg cag gct<br>Gly Gly Pro Glu Pro Lys Pro Gly His Pro Pro Gln Thr Arg Gln Ala<br>                      105                  110                115 | | 990 |
| aca gcc cgg act gtg acc cca aaa gga cag ctt ccc gga ggc aag gca<br>Thr Ala Arg Thr Val Thr Pro Lys Gly Gln Leu Pro Gly Gly Lys Ala<br>          120                    125                  130 | | 1038 |
| ccc cca aaa gca gga tct gtc ccc agc tcc ttc ctg ctg aag aag gcc<br>Pro Pro Lys Ala Gly Ser Val Pro Ser Ser Phe Leu Leu Lys Lys Ala<br>135                        140                    145 | | 1086 |
| agg gag ccc ggg ccc cca cga gag ccc aag gag ccg ttt cgc cca ccc<br>Arg Glu Pro Gly Pro Pro Arg Glu Pro Lys Glu Pro Phe Arg Pro Pro<br>150                        155                    160                165 | | 1134 |
| ccc atc aca ccc cac gag tac atg ctc tcg ctg tac agg acg ctg tcc<br>Pro Ile Thr Pro His Glu Tyr Met Leu Ser Leu Tyr Arg Thr Leu Ser<br>                    170                    175                    180 | | 1182 |
| gat gct gac aga aag gga ggc aac agc agc gtg aag ttg gag gct ggc<br>Asp Ala Asp Arg Lys Gly Gly Asn Ser Ser Val Lys Leu Glu Ala Gly<br>          185                    190                  195 | | 1230 |
| ctg gcc aac acc atc acc agc ttt att gac aaa ggg caa gat gac cga<br>Leu Ala Asn Thr Ile Thr Ser Phe Ile Asp Lys Gly Gln Asp Asp Arg<br>                    200                    205                    210 | | 1278 |
| ggt ccc gtg gtc agg aag cag agg tac gtg ttt gac att agt gcc ctg<br>Gly Pro Val Val Arg Lys Gln Arg Tyr Val Phe Asp Ile Ser Ala Leu<br>215                        220                    225 | | 1326 |
| gag aag gat ggg ctg ctg ggg gcc gag ctg cgg atc ttg cgg aag aag<br>Glu Lys Asp Gly Leu Leu Gly Ala Glu Leu Arg Ile Leu Arg Lys Lys<br>230                        235                    240                245 | | 1374 |
| ccc tcg gac acg gcc aag cca gcg gcc ccc gga ggc ggg cgg gct gcc<br>Pro Ser Asp Thr Ala Lys Pro Ala Ala Pro Gly Gly Gly Arg Ala Ala<br>                    250                    255                260 | | 1422 |
| cag ctg aag ctg tcc agc tgc ccc agc ggc cgg cag ccg gcc tcc ttg<br>Gln Leu Lys Leu Ser Ser Cys Pro Ser Gly Arg Gln Pro Ala Ser Leu<br>                    265                    270                275 | | 1470 |
| ctg gat gtg cgc tcc gtg cca ggc ctg gac gga tct ggc tgg gag gtg<br>Leu Asp Val Arg Ser Val Pro Gly Leu Asp Gly Ser Gly Trp Glu Val<br>          280                    285                  290 | | 1518 |
| ttc gac atc tgg aag ctc ttc cga aac ttt aag aac tcg gcc cag ctg<br>Phe Asp Ile Trp Lys Leu Phe Arg Asn Phe Lys Asn Ser Ala Gln Leu<br>295                        300                    305 | | 1566 |
| tgc ctg gag ctg gag gcc tgg gaa cgg ggc agg gcc gtg gac ctc cgt<br>Cys Leu Glu Leu Glu Ala Trp Glu Arg Gly Arg Ala Val Asp Leu Arg<br>310                        315                    320                325 | | 1614 |
| ggc ctg ggc ttc gac cgc gcc gcc cgg cag gtc cac gag aag gcc ctg<br>Gly Leu Gly Phe Asp Arg Ala Ala Arg Gln Val His Glu Lys Ala Leu<br>                    330                    335                340 | | 1662 |
| ttc ctg gtg ttt ggc cgc acc aag aaa cgg gac ctg ttc ttt aat gag<br>Phe Leu Val Phe Gly Arg Thr Lys Lys Arg Asp Leu Phe Phe Asn Glu<br>345                        350                    355 | | 1710 |

-continued

```
att aag gcc cgc tct ggc cag gac gat aag acc gtg tat gag tac ctg    1758
Ile Lys Ala Arg Ser Gly Gln Asp Asp Lys Thr Val Tyr Glu Tyr Leu
        360             365                 370 ttc agc cag cgg cga aaa cgg cgg gcc cca ctg gcc act cgc cag ggc    1806
Phe Ser Gln Arg Arg Lys Arg Arg Ala Pro Leu Ala Thr Arg Gln Gly
    375                 380                 385 aag cga ccc agc aag aac ctt aag gct cgc tgc agt cgg aag gca ctg    1854
Lys Arg Pro Ser Lys Asn Leu Lys Ala Arg Cys Ser Arg Lys Ala Leu
390                 395                 400                 405 cat gtc aac ttc aag gac atg ggc tgg gac gac tgg atc atc gca ccc    1902
His Val Asn Phe Lys Asp Met Gly Trp Asp Asp Trp Ile Ile Ala Pro
                410                 415                 420 ctt gag tac gag gct ttc cac tgc gag ggg ctg tgc gag ttc cca ttg    1950
Leu Glu Tyr Glu Ala Phe His Cys Glu Gly Leu Cys Glu Phe Pro Leu
            425                 430                 435 cgc tcc cac ctg gag ccc acg aat cat gca gtc atc cag acc ctg atg    1998
Arg Ser His Leu Glu Pro Thr Asn His Ala Val Ile Gln Thr Leu Met
        440                 445                 450 aac tcc atg gac ccc gag tcc aca cca ccc acc tgc tgt gtg ccc acg    2046
Asn Ser Met Asp Pro Glu Ser Thr Pro Pro Thr Cys Cys Val Pro Thr
    455                 460                 465 cgg ctg agt ccc atc agc atc ctc ttc att gac tct gcc aac aac gtg    2094
Arg Leu Ser Pro Ile Ser Ile Leu Phe Ile Asp Ser Ala Asn Asn Val
470                 475                 480                 485 gtg tat aag cag tat gag gac atg gtc gtg gag tcg tgt ggc tgc agg    2142
Val Tyr Lys Gln Tyr Glu Asp Met Val Val Glu Ser Cys Gly Cys Arg
                490                 495                 500 tagcagcact ggccctctgt cttcctgggt ggcacatccc aagagcccct tcctgcactc    2202
ctggaatcac agaggggtca ggaagctgtg gcaggagcat ctacacagct tgggtgaaag    2262
gggattccaa taagcttgct cgctctctga gtgtgacttg gctaaaggc cccctttttat    2322 ccacaagttc ccctggctga ggattgctgc ccgtctgctg atgtgaccag tgcaggcac    2382 aggtccaggg agacagactc tgaatgggac tgagtcccag gaaacagtgc tttccgatga    2442
gactcagccc accatttctc ctcacctggg ccttctcagc ctctggactc tcctaagcac    2502
ctctcaggag agccacaggt gccactgcct cctcaaatca catttgtgcc tggtgacttc    2562
ctgtccctgg acagttgag aagctgactg ggcaagagtg ggagagaaga ggagagggct    2622
tggatagagt tgaggagtgt gaggctgtta gactgttaga tttaaatgta tattgatgag    2682
ataaaaagca aaactgtgcc t                                              2703
```

<210> SEQ ID NO 3
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: aa sequence of human GDF-5; the protein may
      alternatively consist of 119 aa, thus beginning with proline

<400> SEQUENCE: 3

```
Ala Pro Leu Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
        35                  40                  45

Glu Gly Leu Cys Glu Phe Pro Leu Arg Ser His Leu Glu Pro Thr Asn
    50                  55                  60
```

```
His Ala Val Ile Gln Thr Leu Met Asn Ser Met Asp Pro Glu Ser Thr
 65                  70                  75                  80

Pro Pro Thr Cys Cys Val Pro Thr Arg Leu Ser Pro Ile Ser Ile Leu
                 85                  90                  95

Phe Ile Asp Ser Ala Asn Asn Val Val Tyr Lys Gln Tyr Glu Asp Met
            100                 105                 110

Val Val Glu Ser Cys Gly Cys Arg
        115                 120

<210> SEQ ID NO 4
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: aa sequence of monomeric human GDF-5; the
      protein may alternatively consist of 119 aa, thus beginning with
      proline

<400> SEQUENCE: 4

Ala Pro Leu Ala Thr Arg Gln Gly Lys Arg Pro Ser Lys Asn Leu Lys
 1               5                  10                  15

Ala Arg Cys Ser Arg Lys Ala Leu His Val Asn Phe Lys Asp Met Gly
                 20                  25                  30

Trp Asp Asp Trp Ile Ile Ala Pro Leu Glu Tyr Glu Ala Phe His Cys
            35                  40                  45

Glu Gly Leu Cys Glu Phe Pro Leu Arg Ser His Leu Glu Pro Thr Asn
        50                  55                  60

His Ala Val Ile Gln Thr Leu Met Asn Ser Met Asp Pro Glu Ser Thr
 65                  70                  75                  80

Pro Pro Thr Ala Cys Val Pro Thr Arg Leu Ser Pro Ile Ser Ile Leu
                 85                  90                  95

Phe Ile Asp Ser Ala Asn Asn Val Val Tyr Lys Gln Tyr Glu Asp Met
            100                 105                 110

Val Val Glu Ser Cys Gly Cys Arg
        115                 120

<210> SEQ ID NO 5
<211> LENGTH: 102
<212> TYPE: PRT
<213> ORGANISM: Homo sapiens

<400> SEQUENCE: 5

Cys Ser Arg Lys Ala Leu His Val Asn Phe Lys Asp Met Gly Trp Asp
 1               5                  10                  15

Asp Trp Ile Ile Ala Pro Leu Glu Tyr Glu Ala Phe His Cys Glu Gly
                 20                  25                  30

Leu Cys Glu Phe Pro Leu Arg Ser His Leu Glu Pro Thr Asn His Ala
            35                  40                  45

Val Ile Gln Thr Leu Met Asn Ser Met Asp Pro Glu Ser Thr Pro Pro
        50                  55                  60

Thr Cys Cys Val Pro Thr Arg Leu Ser Pro Ile Ser Ile Leu Phe Ile
 65                  70                  75                  80
```

```
Asp Ser Ala Asn Asn Val Val Tyr Lys Gln Tyr Glu Asp Met Val Val
                85                  90                  95

Glu Ser Cys Gly Cys Arg
            100

<210> SEQ ID NO 6
<211> LENGTH: 102
<212> TYPE: PRT
<213> ORGANISM: Homo sapiens

<400> SEQUENCE: 6

Cys Ser Lys Lys Pro Leu His Val Asn Phe Lys Glu Leu Gly Trp Asp
1               5                   10                  15

Asp Trp Ile Ile Ala Pro Leu Glu Tyr Glu Ala Tyr His Cys Glu Gly
            20                  25                  30

Val Cys Asp Phe Pro Leu Arg Ser His Leu Glu Pro Thr Asn His Ala
        35                  40                  45

Ile Ile Gln Thr Leu Met Asn Ser Met Asp Pro Gly Ser Thr Pro Pro
    50                  55                  60

Ser Cys Cys Val Pro Thr Lys Leu Thr Pro Ile Ser Ile Leu Tyr Ile
65                  70                  75                  80

Asp Ala Gly Asn Asn Val Val Tyr Lys Gln Tyr Glu Asp Met Val Val
                85                  90                  95

Glu Ser Cys Gly Cys Arg
            100

<210> SEQ ID NO 7
<211> LENGTH: 102
<212> TYPE: PRT
<213> ORGANISM: Homo sapiens

<400> SEQUENCE: 7

Cys Ser Arg Lys Pro Leu His Val Asp Phe Lys Glu Leu Gly Trp Asp
1               5                   10                  15

Asp Trp Ile Ile Ala Pro Leu Asp Tyr Glu Ala Tyr His Cys Glu Gly
            20                  25                  30

Leu Cys Asp Phe Pro Leu Arg Ser His Leu Glu Pro Thr Asn His Ala
        35                  40                  45

Ile Ile Gln Thr Leu Leu Asn Ser Met Ala Pro Asp Ala Ala Pro Ala
    50                  55                  60

Ser Cys Cys Val Pro Ala Arg Leu Ser Pro Ile Ser Ile Leu Tyr Ile
65                  70                  75                  80

Asp Ala Ala Asn Asn Val Val Tyr Lys Gln Tyr Glu Asp Met Val Val
                85                  90                  95

Glu Ala Cys Gly Cys Arg
            100
```

OPTIMIZED PURIFICATION PROCESS OF RECOMBINANT GROWTH FACTOR PROTEIN

CROSS REFERENCE TO RELATED APPLICATION

This application is a 35 U.S.C. 371 National Phase Entry Application from PCT/EP2008/005016, filed Jun. 20, 2008, which claims the benefit of European Patent Application No. 07 014 798.8 filed on Jul. 27, 2007, the disclosure of which is incorporated herein in its entirety by reference.

DESCRIPTION

This invention relates to an advanced method for the efficient prokaryotic production and purification of recombinant growth factor proteins. More particularly, it is concerned with procedural modifications resulting in a better protein yield, higher product purity and an improved industrial applicability of said process.

Growth and Differentiation Factors (GDF's) are homodimeric cytokines which promote cell proliferation/differentiation and tissue regeneration. A GDF useful over a wide range of medical applications is Growth/Differentiation Factor 5 (GDF-5). Especially the osteogenic properties of GDF-5 have been successfully applied in the past, i.e. to aid the healing of local bone fractures. Very close relatives of GDF-5 with overlapping biological functions and extremely high amino acid homologies are GDF-6 and GDF-7. The GDF-5/-6/-7 group is conserved among mammals but does not have known orthologues in invertebrates (Ducy and Karsenty 2000, Kidney Int. 57, 2207-2214). In In vivo, the members of this protein family are initially synthesized as large precursor proteins which subsequently undergo proteolytic cleavage at a cluster of basic residues approximately 110-140 amino acids from the C-terminus, thus releasing the bioactive C-terminal mature protein parts from the N-terminal prodomain. All mature polypeptides are structurally related and contain a conserved bioactive domain comprising six or seven canonical cysteines. Disulfide bridges between those residues contribute to the typical three-dimensional "cystine-knot" motif of this protein family.

Expression of mature GDF-5 in prokaryotic hosts has already been achieved in the past (see e.g. Biochem. Biophys. Res. Commun., 204, pp. 646-652, 1994). However, these proteins cannot be easily prepared in a purified form.

When expressed in large scale in $E.\ coli$, the desired protein generally tends to form a monomeric and inactive protein with a size of 14 kDa which is accumulated in inclusion bodies. In order to obtain the dimeric bioactive growth factor (28 kDa), the monomeric inclusion body protein must be solubilized, purified and renatured to a homodimer with the typical cystine-knot structure. This procedure is generally called "refolding".

Due to an extremely low solubility in aqueous solutions of pH values between pH 4 and pH 9 as well as other uncommon protein characteristics, the purification and refolding of GDF-5 related proteins which are produced in prokaryotes necessarily involves several specifically adapted procedural steps. For example, since refolded GDF-5 related proteins tend to adsorb onto a chromatographic resin, it has become apparent that the purification of the desired protein in large-scale production can not be accomplished according to standard purification protocols and aqueous chromatographic components. Once the protein is refolded, primarily purification methods which are utilizing organic solvents (such as reverse phase chromatography) are applicable.

A recently developed production and purification process of recombinantly produced GDF-5 related proteins is disclosed in WO 96/33215. The method is based upon purification of the monomeric protein prior to the refolding procedure and comprises the following principle steps:
1. bacterial culture, cell disruption and recovery of inclusion bodies,
2. treatment with a denaturing agent to obtain solubilized monomer,
3. separation by ion exchange chromatography,
4. sulfonation (the sulfonation step is optional),
5. separation by gel filtration chromatography,
6. refolding,
7. recovery by isoelectric precipitation, and
8. separation by reverse-phase chromatography.

Although the procedure as described above is basically applicable, the method has encountered some difficulties in the first two processing steps that affect both yield and purity of the target protein. The obtainable GDF-5 related protein yield is significantly lower as theoretically expected, mainly due to partial degradation events in connection with an uncommonly turbid/viscous solution during the solubilization of the inclusion body protein. Thus, it is obvious that the disclosed process parameters and conditions should be improved.

Objects of this invention are to overcome the above-mentioned problems and to optimize the yield and purity of recombinant GDF-5 related proteins.

These objects are solved by the development of advanced methods disclosed hereinafter for the production of recombinant GDF-5 related proteins in $E.\ coli$.

Prior to the detailed description of the invention, some frequently used terms should be defined and exemplified as follows:

The term "cystine-knot domain" as used herein means the well known and conserved cysteine-rich amino acid region which is present in the mature parts of TGF-beta superfamily proteins such as i.e. human GDF-5 and forms a three-dimensional protein structure known as cystine-knot. In this domain the respective location of the cysteine residues to each other is important and is only allowed to vary slightly in order not to lose the biological activity. It has been demonstrated that the cystine-knot domain alone is sufficient for the biological function of the protein (Schreuder et al. (2005), Biochem Biophys Res Commun. 329, 1076-86). Consensus sequences for cystine-knot domains are well known in the state of the art. According to the definition defined herein the cystine-knot-domain of a protein starts with the first cysteine residue participating in the cystine-knot of the respective protein and ends with the residue which follows the last cysteine participating in the cystine-knot of the respective protein. For example, the cystine-knot domain of the human GDF-5 precursor protein (SEQ ID NO: 1) consists of the amino acids 400-501 (see also FIG. 1).

The term "GDF-5-related protein" as used herein means any naturally occurring or artificially created protein which comprises a cystine-knot-domain with an amino acid identity of at least 60% to the 102 aa cystine-knot domain of human GDF-5 (amino acids 400-501 of SEQ ID NO: 1). This term includes proteins with similar biophysical properties which are belonging to the group of GDF-5, GDF-6 and GDF-7 proteins from vertebrate or mammalian species as well as recombinant variants thereof, as long as these proteins show the above mentioned percentage of identity with the cystine-knot domain of human GDF-5. The limiting value of 60% is well suitable to separate members of the GDF-5/-6/-7 group of proteins as well as variants thereof from further proteins such as other GDFs and BMPs. A comparison of the 102 aa cystine-knot-domains of human GDF-5, human GDF-6 and human GDF-7 (see FIG. 2) reveals the high grade of amino acid identity between these proteins. Human GDF-6 shares 87 (85%) and human GDF-7 shares 83 (81%) identical residues with the cystine-knot-domain of human GDF-5. The respective domains of GDF-5/-6/-7 molecules from other vertebrate and mammalian species which have been identified so far also show very high identity percentages of at least 75% (between 79% and 99%), when compared with human GDF-5. In contrast, GDFs and BMPs not belonging to the GDF-5/-6/-7 subgroup display much lower identity values below 60% (see FIG. 3)

The determination of corresponding amino acid positions in related amino acid sequences as well as the calculation of percentages of identity between can be easily performed with the help of well known alignment algorithms and optionally computer programs using these algorithms. For example, the amino acid identities in this patent application (i.e. FIG. 2) have been calculated by aligning sequences with the freeware program ClustalX (Version 1.81) with default parameters and subsequent counting of identical residues by hand. Default settings for pairwise alignment (slow-accurate) are: gap opening parameter: 10.00; gap extension parameter 0.10; Protein weight matrix: Gonnet 250. The ClustalX program is described in detail in Thompson, J. D., Gibson, T. J., Plewniak, F., Jeanmougin, F. and Higgins, D. G. (1997):

The ClustalX windows interface: flexible strategies for multiple sequence alignment aided by quality analysis tools.

Nucleic Acids Research 24:4876-4882.

ClustalX is a windows interface for the ClustalW multiple sequence alignment program and is i.e. available from various sources, i.e. by anonymous ftp from ftp-igbmc.u-strasbg.fr, ftp.embl-heidelberg.de, ftp.ebi.ac.uk or via download from the following webpage: www-igbmc.u-strasbg.fr/BioInfo/. The ClustalW program and algorithm is also described in detail in Thompson, J. D., Higgins, D. G. and Gibson, T. J. (1994):

CLUSTALW: improving the sensitivity of progressive multiple sequence alignment through sequence weighting, positions-specific gap penalties and weight matrix choice.

Nucleic Acids Research 22:4673-4680.

The term "variant" as used herein means any of the following polypeptides:
a) biologically active fragments of a protein
b) biologically active protein constructs which contain additional sequences in excess to the original sequence of the protein
c) any combination of a) and b)

The terms "dissolution buffer" or "solubilization buffer" of inclusion bodies mean solutions which are used for the solubilization of inclusion bodies and the denaturation of the protein incorporated in said inclusion bodies.

The term "biological activity" denotes the activity of therapeutic compounds, including, e.g., a GDF-5-related protein as measured by the common in vitro alkaline phosphatase assay (ALP), e.g. as described in example 5 or in Takuwa et al. (1989), Am. J. Physiol. 257, E797-E803). Suitable cell lines which may be used in such ALP assay are e.g. ATDC-5 or MCHT 1/26 cells.

In the following a more detailed description of the invention is given:

The manufacturing method of recombinant GDF-5 related proteins and particularly of recombinant human GDF-5 comprises the initial steps of fermentation in E. coli, harvest of biomass, cell disruption, inclusion body collection/washing and inclusion body dissolution under denaturing conditions. Subsequently the denatured protein is subjected to downstream purification steps and a refolding procedure as e.g. described in WO 96/33215.

The mentioned cell disruption step is routinely done by using a high-pressure homogenizer. Afterwards, the inclusion bodies (IB's) are usually collected by centrifugation and (optionally) repeatedly washed. Thorough dissolution (solubilization) of the inclusion body protein prior to the subsequent purification steps is achieved by suspension in a solubilization buffer comprising high amounts of denaturing urea.

Remarkably, the solubilization solution now containing the monomeric and denatured inclusion body protein appears to be extremely turbid and viscous, even after previous filtration or centrifugation. At the same time, a time-dependant fragmentation of the monomeric GDF-5 is occurring (see FIG. 5), a process which ultimately leads to a destruction/size reduction of a significant part of the GDF-5 monomer. In less than 1.5 hours, the size of the mature monomeric protein is considerably reduced from originally 14 kD to approximately 10 kD in the dissolution solution. This undesired and fast degradation event seems to be sequence-/conformation-related and is restricted to the step of inclusion body solubilization. The time-dependant degradation process interferes especially with the protein production in large/industrial scales since processing times are usually extended as a result of the upscaled quantities. In consequence, the yield and purity of the GDF-5 related protein finally obtained after the whole purification procedure is significantly reduced.

In order to overcome the disclosed problems, the inventors have made substantial investigations and pursued a variety of different approaches which finally resulted in a modified purification process. These attempts included variations of the cell disruption procedure, protease inactivation experiments in order to combat a potential enzymatic/proteolytic contamination, amendments of the concentration of critical solubilization and/or washing buffer components, and addition of different chemical compounds to the solubilization buffer.

Whereas different efforts with the subject to verify and inactivate a putative proteolytic activity contributing to the observed protein degradation all failed (see example 3: Chemical inhibition and heat inactivation), the inventors have found that a reduction of protein fragmentation and a higher protein yield/purity can nonetheless be achieved by the implementation of two important process-related modifications, either alone or (preferably) in combination. These modifications are specific embodiments of the disclosed invention and relate to 1) the adaptation of the cell disruption procedure and 2) to the optimization of the solubilization buffer composition. They are exemplified hereinafter in more detail:

1) Modification of Cell Disruption by High Pressure Homogenization

It has been determined that the unusual high turbidity and viscosity of the solubilization solution (comprising the solubilized inclusion bodies) is detrimental for the downstream purification process of GDF-5 related proteins and must be avoided. Whereas neither additional filtration nor centrifugation steps prior to the inclusion body solubilization could solve the problem, this issue was unexpectedly found to be addressable by a very selective modification of the applied cell disruption pressure. Whereas this pressure is usually variable over a wide range (e.g. from 100 to 2000 bar) without dramatic impacts on the inclusion body solubilization, it is imperative to limit this pressure to a narrow range if GDF-5 related proteins are purified. More precisely, if a disruption pressure between 800-900 bar is applied, a significant clearer solution of solubilized inclusion bodies and an increase of product yield during the first part of the purification process of GDF-5 related proteins is detectable. Furthermore, the ratio (rhGDF-5/total protein) is considerably improved at the higher disruption pressure. Because of the better filterability the overall processing time is shorter and thus the time-dependant protein fragmentation is reduced. In contrast, disruption pressures above or below this range are detrimental and lead to significant yield reductions (see for example FIG. 6).

2) Modifications of the Solubilization Buffer Composition

The following modifications of solubilization buffer components are covered by this invention:

Urea/Supplementation with L-Arginine

Although a detrimental effect of urea on the stability of the primary structure of Growth and Differentiation Factors (GDF's) is not described in the prior art, it has been discovered by the inventors that the fragmentation of GDF-5 related proteins does not occur if urea is completely removed from all solutions (e.g. from washing and solubilization buffers) which are in contact with the inclusion bodies. However, elimination of a denaturing agent from solubilization buffers is not feasible in order to maintain the desired denaturing effect. Unfortunately, substitution of urea by guanidine hydrochloride (GuHCl) as an alternative denaturant is also not recommendable in industrial production plants due to the corrosion-supporting attributes of guanidine salts (which may in some cases lead to a reduced economic life-time of pipes and tanks). Furthermore GuHCl is very expensive and may boost the process-related costs.

The inventors have therefore looked for an alternative way to eliminate the aforementioned protease related GDF-5 decay. As a result of detailed experimentation, it was found that said fragmentation of GDF-5 related proteins can be eliminated in urea-containing solubilization buffers, if said solutions are supplemented with defined concentrations of L-arginine as a protective additive.

As shown in example 3/FIGS. 7 and 8, addition of L-arginine to urea-containing solutions reduces or eliminates the degradation of GDF-5 in a concentration-dependant manner. Degradation could be reduced by approximately 50 percent with buffers containing at least 100 mM L-arginine, and it is stopped completely by using dissolution buffers containing 500 mM L-arginine or more. Even minor concentrations of L-Arginine (such as 1 mM L-Arginine in buffer A4 of example 3) display a detectable fragmentation-inhibiting effect.

The use of L-arginine as a supplementary ingredient for urea-containing solubilization buffers of inclusion bodies containing GDF-5 related proteins has several advantages. First, since L-arginine is a comparatively low-priced chemical product, the cost-effectiveness of the protein purification process is maintained despite the addition of this substance. Second, a combination of urea and L-arginine is much less corrosive than a denaturing solution comprising guanidine hydrochloride. Third, L-arginine is more environmentally friendly compared to guanidinium salts that require special disposal. This advantage makes the invention especially useful for industrial plants with metal-rich devices. Furthermore L-arginine can easily be removed from the purification process by applying a simple diafiltration step, e.g. directly after the solubilization of the inclusion bodies. This is especially important since the proposed addition of L-arginine to the solubilization buffer interferes with the subsequent binding of GDF-5 related proteins to the ion exchange chromatography (IEC) column. (see example 4). Diafiltration and IEC are facilitated if additional purification steps (e.g. centrifugation, depth filtration and/or sterile filtration) are (optionally) applied after the inclusion body solubilization in order to remove high molecular weight contaminants such as cellular debris. Possible pore size parameters for the depth filtration are e.g. 0.1-0.7 µm, for the sterile filtration e.g. 0.22 µm.

Thus, according to a preferred embodiment of the invention and in order to prevent protein fragmentation/degradation, a solubilization buffer for the treatment of inclusion bodies of GDF-5 related proteins should contain L-arginine. The preferred concentration of this additive ranges from 100 to 1000 mM L-arginine in the solubilization buffers of the invention. The most preferred concentration is 400 to 500 mM L-arginine. However, it is also possible to use higher concentration of L-arginine (e.g. up to 2000 mM) which might be useful in case of extremely long incubation/processing periods.

Solubilization buffers of the inventions are further characterized to contain between 2 and 10M urea as denaturing agent. Preferably, the concentration of urea ranges between 4M and 8M. Most preferred is a solubilization buffer comprising 6M urea.

Other parts of the invention relate to further modifications of said solubilization buffers which have less dramatic but nonetheless significant effects on the process productivity.

pH:

According to the rhGDF-5 purification process disclosed in WO1996/033215, a pH of 8.3 is described as suitable for a solubilization buffer of GDF-5 related proteins. However, it has now been found (see also example 3/FIG. 7) that the use of solubilization buffers with higher pH values between 9.0 and 11.0 helps to reduce degradation and improves the amount of total protein obtained in the purification process. This finding might be explained with the pH-dependant solubility profile of GDF-5 which is shown in FIG. 9. The solubility is low at pH 8.3 but increases significantly with higher pH. Thus, a pH between 9.0 and 11.0 is also considered to be useful for the solubilization buffers of the invention.

Chelators:

Also the concentration of chelators in the solubilization buffers might me adapted. Chelators are employed to safely bind with metal agents such as mercury, arsenic, or lead. A commonly used synthetic chelator is EDTA which is used in the solubilization buffers of the invention (e.g. in form of $Na_2EDTA$ or $Na_3EDTA$). According to the experiments described in example 3, it is beneficial to increase the concentrations of chelators from the originally described 1 mmol/l (see WO/1996/033215) to 5-100 mmol/l, preferably to 5-50 mmol/l.

The most preferred solubilization buffer comprises the following components:

20 mM Tris-HCl
6M Urea
64 mM DTT
500 mM L-arginine
5 mM $Na_3EDTA$

Major process modifications according to the invention are summarized in FIG. 10. It should be noted by way of precaution that the proposed purification scheme represents a preferred embodiment of the invention but that the invention is in no way limited to this order or number of processing steps (especially concerning steps 5 to 9 of FIG. 10). Single steps may be omitted, substituted or supplemented with other purification methods, as long as the whole purification procedure comprises the initial steps of 1. bacterial cell culture (preferred bacterial host is *E. coli*, especially preferred host strains are W3110 and D1210, 2. cell disruption, 3. recovery of inclusion bodies and 4. solubilization of inclusion bodies.

The disclosed invention has been exemplified with recombinant human GDF-5 as test substance. However, due to an extraordinary high sequence homology (see FIG. 2) the purification methods can also be applied to the purification of other GDF-5 related proteins. The term "GDF-5-related proteins" includes functionally similar proteins belonging to the group of vertebrate GDF-5, GDF-6 and GDF-7 proteins as well as recombinant variants thereof. Common feature of all GDF-5-related proteins is the occurrence of a bioactive cystine-knot-domain with an amino acid identity of at least 60% to the 102 aa cystine-knot domain of human GDF-5 which is sufficient for the biological function of the protein. As can be seen from FIG. 3, the preferred limiting value of 60% separates members of the GDF-5/-6/-7 group from more distantly related GDFs and BMPs. Especially preferred proteins display amino acid identities of at least 75%, 80% or 90% to the 102 aa cystine-knot domain of human GDF-5.

Non-limiting examples for vertebrate and mammalian GDF-5-related proteins are precursors and mature proteins of human GDF-5 (disclosed as MP52 in WO95/04819 and as human GDF-5 in Hötten et al. 1994, Biochem. Biophys Res. Commun. 204, 646-652), recombinant human GDF-5/MP52 (WO96/33215), MP52 Arg (WO97/06254); HMW human MP52s (WO97/04095), CDMP-1 (WO96/14335), mouse (*Mus musculus*) GDF-5 (U.S. Pat. No. 5,801,014), rabbit (*Oryctolagus cuniculus*) GDF-5 (Sanyal et al. 2000, Mol. Biotechnol. 16, 203-210), chicken (*Gallus gallus*) GDF-5 (NCBI accession no. NP_989669), african clawed frog (*Xenopus laevis*) GDF-5 (NCBI accession no. AAT99303), monomeric GDF-5 (WO 01/11041 and WO 99/61611), human GDF-6/BMP-13 (U.S. Pat. No. 5,658,882), mouse GDF-6 (NCBI accession no NP_038554), GDF-6/CDMP-2 (WO96/14335), human GDF-7/BMP-12 (U.S. Pat. No. 5,658,882), mouse GDF-7 (NCBI accession no AAP97721), GDF-7/CDMP-3 (WO96/143335). Covered by the invention are also GDF-5-related proteins having additional mutations such as substitutions, additions and deletions, as long as these additional mutations do not completely abolish the biological protein activity. Some preferred variants are mutants of GDF-5-related proteins with improved biological activity. For example, one or more residues which are normally present in the human GDF-5 precursor protein (see FIG. 1) are substituted in these mutants by other amino acids: the arginine at position 438 of the human GDF-5 precursor is replaced by glycine, alanine, valine, leucine, isoleucine, methionine or asparagines; and/or serine 439 is replaced by aspartic acid, glutamic acid, glycine, leucine, or isoleucine; and/or asparagine 445 is replaced by serine or threonine. In another high activity mutant, methionine 453 and/or methionine 456 are replaced by alanine, valine, or isoleucine. Also of special interest are mutants in which leucine 441 is replaced by proline.

The biological activities of GDF-5-related proteins can be easily determined with the help of established test systems. Most useful and preferred is a common in vitro test known as alkaline phosphatase (ALP) assay (Takuwa et al. 1989, Am. J. Physiol. 257, E797-E803), which is also described in example 5. GDF-5-related proteins have been demonstrated to increase alkaline phosphatase activity i.e. in ROB-C26 cells (Yamaguchi et al. 1991, Calcif. Tissue Int. 49, 221-225) as described in WO95/04819, in embryonic ATDC5 cells (Riken Gene Bank, ROB 0565), in mouse stromal MCHT-1/26 cells, and in HPDL cells as shown in Nakamura et al. 2003, J. Periodontal Res. 38, 597-605.

The following non-limiting examples together with the figures and sequence protocols are intended to further illustrate the invention.

SEQUENCES

SEQ ID NO:1 shows the protein sequence of the human GDF-5 precursor.

SEQ ID NO:2 shows the DNA sequence of the human GDF-5 precursor.

SEQ ID NO:3 shows the 120 aa protein sequence of mature human GDF-5. If recombinantly produced, the protein may alternatively consist of 119 aa, thus beginning with the second aa (proline) of SEQ ID NO:3.

SEQ ID NO:4 shows the 120 aa protein sequence of mature human monomeric GDF-5. The protein may alternatively consist of 119 aa, thus beginning with the second aa (proline) of SEQ ID NO:4.

FIGURES

FIG. 1 shows additional features of the human GDF-5 precursor protein according to SEQ ID NO:1:
aa 001-381 pre-prodomain (bold letters)
aa 001-027 signal peptide (bold and underlined)
aa 382-501 mature protein part
aa 400-501 cystine-knot-domain (underlined)

FIG. 2 shows a comparison of the 102 aa cystine-knot domains of human GDF-5 (human GDF-5 precursor protein: SEQ ID NO: 1; cystine-knot domain of human GDF-5: SEQ ID NO: 5), human GDF-6 (sequence 2 from U.S. Pat. No. 5,658,882; here SEQ ID NO: 6) and human GDF-7 (sequence 26 from U.S. Pat. No. 5,658,882; here SEQ ID NO: 7). Amino acid residues which are identical in all three molecules are highlighted.

FIG. 3 shows a table with the sequence identities of cystine-knot domains of several known BMPs and GDFs to the cysteine-knot-domain of human GDF-5.

FIG. 4 shows a plasmid map for the expression of recombinant human mature GDF-5 as described in example 1 and (more detailed) in WO 1996/033215.

FIG. 5 shows an SDS-Page displaying the time-dependant fragmentation of recombinant mature GDF-5 during inclusion body solubilization in solubilization buffer (8 M urea, 20 mM Tris, 10 mM DTT, 1 mM $Na_2EDTA$, pH 8.3). Monomeric GDF-5 is reduced from 14 kDa to 10 kDa (fragment). Fragmentation is nearly complete after 3 hours of solubilization.

FIG. 6 shows an SDS-Page displaying the effect of cell disruption pressure modification on protein fragmentation, yield and purity according to example 2. In this subset of the experiment, a disruption pressure of 560 bar (upper picture) is compared with a disruption pressure of 850 bar (lower picture). The higher pressure of 860 bar leads to a significant decrease of protein fragmentation and a higher protein yield/purity.

FIGS. 7 and 8 show an SDS-Page displaying the effects of different solubilization buffers on the fragmentation of monomeric GDF-5 dissolved in the solubilization buffer. Buffer compositions are listed in example 3.

FIG. 9 shows a pH-dependant solubility profile of mature GDF-5

FIG. 10 shows modifications of the GDF-5 production process according to the invention.

EXAMPLES

Example 1

Production and Purification of rhGDF-5

(1) Construction of an Expression Vector and Transformation of *E. coli*

The construction of a plasmid vector system for the production of mature recombinant human GDF-5 (amino acids 1 to 119 of Seq ID No. 3) and transformation of host strain *E. coli* W3110 (W3110M) was performed as described in example 1 of WO 1996/033215.

(2) Cultivation in *E. coli*

The *E. coli* expressing the protein of the invention was precultured in the modified SOC medium (Bacto tryptone 20 g/l, Bacto yeast extract 5 WI, NaCl 0.5 g/l, $MgCl_2.6H2O$ 2.03 g/l, Glucose 3.6 g/l). 100 ml of the bacteria suspension was used to inoculate 5 l of the production medium (Bacto tryptone 5 g/l, Citric acid 4.3 g/l, $K_2HPO_4$ 4.675 g/l, $KH_2PO_4$ 1.275 g/l, NaCl 0.865 g/l, $FeSO_4 \times 7H_2O$ 100 mg/l, $CuSO_4 . \times 5H_2O$ 1 mg/l, $MnSO_4.xnH_2O$ 0.5 mg/l, $CaCl_2 \times 2H_2O$ 2 mg/l, $Na_2B_4O_7 \times 10H_2O$ 0.225 mg/l, $(NH_4)_6Mo_7O_{24} \times 4H_2O$ 0.1 mg/l, $ZnSO_4 \times 7H_2O$ 2.25 mg/l, $CoCl_2 \times 6H_2O$ 6 mg/l, $MgSO_4 \times 7H_2O$ 2.2 g/l, Thiamine HCl 5.0 mg/l, Glucose 3 g/l), which was cultured in a 10-liter fermenter with aeration-agitation, and then upon reaching the early stage of logarithmic growth phase (OD550=5.0), isopropyl-beta-D-thio-galactopyranoside at a final concentration of 1 mM was added and the cultivation was continued until reaching OD550=150. During the cultivation, temperature was kept at 32° C., and pH value of 7.15 by adding ammonia. In order to prevent lowering of a dissolved oxygen concentration, an agitation was sped up to keep the dissolved oxygen concentration at 50% of air saturation. The cultivation was proceeded by adding 50% glucose solution at a level of 0.2% to obtain a high cell density, with an indication of abrupt increase of the dissolved oxygen concentration.

(3) Preparation of *E. coli* Inclusion Bodies

The culture broth obtained by the method described above was centrifuged to harvest the cells, which were then suspended in 25 mM Tris-HCl buffer containing 10 mM ethylene diamine tetraacetic acid (pH 7.3). The cells were disrupted by passing through a high pressure homogenizer and centrifuged again to harvest the precipitate containing the inclusion bodies.

(4) Washing and Solubilization of *E. coli* Inclusion Bodies

After washing (e.g. with 1% Triton X-100) three times, the *E. coli* inclusion bodies were centrifuged at 3,000×g for 30 minutes at 4° C., and then the resultant precipitate was solubilized by sonication in solubilization buffer (20 mM Tris-HCl buffer, 8 M urea, 10 mM DTT, and 1 mM $Na_2EDTA$, pH 8.3). Due to the observed partial degradation of GDF-5 inclusion body protein in urea-containing buffers (see FIG. 5), a variety of additional solubilization buffers have also been tested which are described in example 3.

(5) Preparation of Monomers

The solubilized solution was centrifuged at 20,000×g for 30 minutes at 4° C. and the resultant supernatant was collected. The obtained supernatant was subjected to SP-Sepharose FF (Pharmacia AB) equilibrated with 20 mM Tris-HCl buffer pH 8.3, 6 M urea, and 1 mM EDTA, and then, after washing with the same solution, it was eluted with the same solution containing 0.5 M NaCl. The protein in the eluate were sulfonated by adding $Na_2SO_3$ and $Na_2S_4O_6$ to read the final concentration respectively at 111 mM and 13 mM and by incubating at 4° C. for 15 hours. The sulfonated solution was gel-filtrated on Sephacryl S-200 HR (Pharmacia AB) equilibrated with 20 mM Tris-HCl buffer, pH 8.3, 6 M urea, 0.2 M NaCl, and 1 mM EDTA to obtain purified sulfonated monomers of the protein of the invention.

(6) Refolding

The solution of the sulfonated monomers was added into a 9 times volume of 50 mM Na-Glycine buffer pH 9.8, 0.2 M NaCl, 16 mM CHAPS, 5 mM EDTA, 2 mM GSH (reduction type glutathione), and 1 mM GSSG (oxydation type glutathione) with stirring, and then incubated for 24 hours at 4° C. to oxidize and refold the protein of the invention.

(7) Preparation of Homodimers

The refolding solution was diluted with the same volume of purified water and then by adding 6 N NaCl adjusted pH value to approximately 7.4 and placed to isoelectric precipitation. The precipitates collected by centrifugation at 3,000×g for 20 minutes were solubilized in a solution with 30% acetonitrile containing 0.1% TFA. The solution was diluted with the same volume of purified water and loaded on RESOURCE RPC column (Pharmacia AB) of a reverse-phase HPLC preequilibrated with 25% acetonitrile containing 0.05% TFA, and then eluted with a linear gradient of 25-45% acetonitrile containing 0.05% TFA. The eluate was monitored at 280 nm absorbance. The purified homodimer protein fractions were collected and lyophilized by SpeedVac Concentrator (Servant Co.). Optionally, the purified protein was subjected to a final ultra-/diafiltration step.

Example 2

Variations 1—Modification of the Cell Disruption Pressure

In order to evaluate the effect of cell disruption on protein yield/degradation, purity and filterability, several experiments with different cell disruption pressures were performed.

The biomass of each fermentation was resuspended in homogenization buffer (25 mM Tris, 10 mM $Na_2EDTA$, pH 7.3), homogenized and stirred for 30 to 60 minutes with a magnetic stirrer. Subsequently, the biomass suspension was disrupted in a high pressure homogenizer three times at different disruption pressures. The received inclusion bodies were washed with washing buffer (20 mM Tris, 5 mM $Na_2EDTA$ pH 8.3) and stored at <−70° C. After thawing over night at 4° C., the IBs were dissolved in precooled solubilization buffer containing 6 M Urea and 0.5 M L-arginine, homogenized and stirred again with a magnetic stirrer for 30 to 60 minutes. Afterwards the IB solution was centrifuged for 30 minutes at 10° C., g-force 10000×g (=7500 rpm). The supernatant was decanted to separate the IBs from the insoluble components, and filtered through depth filters (CUNO Zeta Plus BC0030A90ZA08A). Afterwards the filtrate was filtered again through a sterile filter (Nalgene Bottle Top Filter 0.2 μm). The sterile filtrate was concentrated and diafiltrated against CEX Buffer A (6 M Urea, 20 mM Tris, 1 mM $Na_2EDTA$, 50 mM NaCl, 10 mM DTT, pH 8,3) before loading on the CEX column. Test samples generated by the different steps were analyzed with known analytical test methods such as SDS-PAGE, Coomassie-Brilliant-Blue stain and ELISA-techniques for the determination of *E. coli* proteins.

The results of this investigation (see FIG. 6) show that a significant improvement of the primary purification process of rhGDF-5 can be achieved if cell disruption is done with a disruption pressure between 800 and 900 bar. A better quality of IB's is obtained, resulting in a higher ratio of rhGDF-5/ total protein (e.g. 57% at 850 bar vs. 35% at 560 bar) and a reduced content of E. coli proteins for the final product (e.g. ≦30 µg/mg at 850 bar vs.>50 µg/mg at 560 bar). These improvements are also beneficial for the filterability. The needed filter area for the production scale could be reduced (e.g. from theoretical 2.6 m² at 560 bar to <1 m² at 850 bar) in large scale. This leads to lower process time, a reduced fragmentation of the protein and to a cut of the corresponding rhGDF-5 production costs.

Example 3

Variations II—Inclusion Body Solubilization

In order to prevent the degradation of GDF-5 and related proteins, the standard step of inclusion body solubilization as e.g. described in example 1 was altered in different aspects. Efforts comprised experiments to identify/inhibit a potential proteolytic activity as well as amendments of the composition of the solubilization buffer as described in example 1 (e.g. pH, urea, Na₂EDTA and DTT, GuHCl, amino acids such as L-arginine).
(3.1) Protease Inhibition Experiments
(3.1.1) Chemical Inhibition
In this set of experiments a protease inhibitor cocktail was used. In a subgroup, inclusion bodies were additionally resuspended for 20 min in 25% HCl (pH 2.7) in order to inactivate proteases which are bound to the outer cell wall. After 3 washing steps, 8 g of recombinant human GDF-5 (rhGDF-5) inclusion bodies were dissolved in 50 ml standard solubilization buffer containing 8M urea. 2 tablets containing a mixture of protease inhibitors (Roche Diagnostics Protease Inhibitor Cocktail Tablets Cat. No. 11 697 498 001) were added and thoroughly mixed with the inclusion body solution. After 1.5 h and 3 h of incubation at RT, samples were centrifuged and analyzed. rhGDF-5 was found to be largely degraded in all groups, indicating that chemical inhibition of protein degradation by the use of HCl or protease inhibitors is ineffective.
(3.1.2) Heat Inactivation
After 3 washing steps, 15 g of recombinant human GDF-5 (rhGDF-5) inclusion bodies were dissolved in 100 ml buffer containing 10 mM Na₂EDTA, 25 mM Tris (pH 7.3). Thermal inactivation was done by incubation at 65° C. over different time periods (20 min to 2 hours). Afterwards, samples were subjected to a standard solubilization step as described in example 1. Results: Despite the thermal inactivation of proteases, rhGDF-5 was degraded in all these samples.
(2) Amendments of Solubilization Buffer Compositions.
Attempts to minimize the fragmentation of GDF-5 related proteins by modification of the used solubilization buffer were successful. Some of the tested solubilization buffers are listed below:
Buffers with Urea:
Standard: 8 M urea, 20 mM Tris, 10 mM DTT, 1 mM Na₂EDTA, pH 8.3
Buffer U1: 8 M urea, 20 mM Tris, 64 mM DTT, 50 mM Na₂EDTA, pH 8.3
Buffer U2: 6 M urea, 20 mM Tris, 64 mM DTT, 50 mM Na₂EDTA, pH 8.3
Buffer U3: 6 M urea, 20 mM Tris, 64 mM DTT, 5 mM Na₂EDTA, pH 8.3
Buffer U4: 6 M urea, 20 mM Tris, 64 mM DTT, 5 mM Na₂EDTA 50 mM NaCl, pH 8.3
Buffer U5: 6 M urea, 20 mM Tris, 64 mM DTT, 5 mM Na₂EDTA, pH 9.5

Buffers with L-arginine:
Buffer A1: 100 mM arginine, 6 M urea, 20 mM Tris, 64 mM DTT, 5 mM Na₂EDTA, pH 8.3
Buffer A2: 30 mM arginine, 6 M urea, 20 mM Tris, 64 mM DTT, 5 mM Na₂EDTA, pH 8.3
Buffer A3: 10 mM arginine, 6 M urea, 20 mM Tris, 64 mM DTT, 5 mM Na₂EDTA, pH 8.3
Buffer A4: 1 mM arginine, 6 M urea, 20 mM Tris, 64 mM DTT, 5 mM Na₂EDTA, pH 8.3
Buffer A5: 200 mM arginine, 6 M urea, 20 mM Tris, 64 mM DTT, 5 mM Na₂EDTA, pH 8.3
Buffer A6: 100 mM arginine, 6 M urea, 20 mM Tris, 64 mM DTT, 5 mM Na₂EDTA, pH 9.5
Buffer A7: 500 mM arginine, 6 M urea, 20 mM Tris, 64 mM DTT, 5 mM Na₂EDTA, pH 9.5
Buffer A8: 500 mM arginine, 6 M urea, 20 mM Tris, 64 mM OTT, 5 mM Na₂EDTA, pH 8.3
Buffer A9: 300 mM arginine, 6 M urea, 20 mM Tris, 64 mM DTT, 5 mM Na₂EDTA, pH 8.3
Buffer A10: 400 mM arginine, 6 M urea, 20 mM Tris, 64 mM DTT, 5 mM Na₂EDTA, pH 8.3

For degradation testing, 0.1 g GDF-5 inclusion bodies were mixed with 0.9 ml solubilization buffer. Degradation was checked after 4-5 hours incubation of inclusion bodies dissolved in solubilization buffer. Results were analysed by SDS-Page and subsequent staining with Coomassie Brilliant Blue.

Results: Inter alfa, the following results were achieved during degradation tests:
- Na₂EDTA: increase of concentration from 1 to 5-50 mM leads to a slight reduction of degradation
- pH: a change from 8.3 to higher values (between 9.0 and 11.0) leads to a reduction of degradation as well as to an increase of the amount of total protein. For example, elevation of the pH from 8.3 to 9.5 in the solubilization buffers (see e.g. buffers A7 and A8 in FIG. 7) did improve both the amount of total protein and the grade of degradation. Even IBs dissolved in buffers containing low amounts of L-arginine still contained rhGDF-5 after 5 hrs of incubation at RT if the pH was increased (see e.g. buffer A6 in FIG. 7).
- DTT: alteration without effect
- Amino acids, especially L-arginine: The following initial results were achieved with solubilization buffers containing 0 to 100 mM L-Arginine (pH 8.3):

| Used buffer | Incubation time | Degradation of rhGDF-5 |
| --- | --- | --- |
| Buffer without Arg (ref.) | 0 hrs incubation | nearly complete |
|  | 4 hrs incubation at RT | nearly complete |
| Buffer A1 | 0 hrs incubation | about 50% |
|  | 4 hrs incubation at RT | about 50% |
| Buffer A3 (30 mM L-Arg, pH 8.3) | 0 hrs incubation | about 50% |
|  | 4 hrs incubation at RT | nearly complete |
| Buffer A2 (10 mM L-Arg, pH 8.3) | 0 hrs incubation | about 50% |
|  | 4 hrs incubation at RT | nearly complete |
| Buffer A4 (1 mM L-Arg, pH 8.3) | 0 hrs incubation | Degradation less than in reference sample |
|  | 4 hrs incubation at RT | nearly complete |

In subsequent experiments a higher L-arginine concentration was used. The incubation time was increased to 5 hrs. Scope of this experiment was to test the influence of a) a higher L-Arginine concentration in the dissolution buffer and b) a pH shift to more basic conditions on rhGDF-5 degradation. Results were:

| Used buffers | Total protein [mg/ml] | rhGDF-5 [mg/ml] | rhGDF-5 ratio [rhGDF-5/total protein] | Degradation of rhGDF-5 |
|---|---|---|---|---|
| Buffer without Arg (pH, 8.3) | 5.92 | no rhGDF-5 found[1] | no rhGDF-5 found[1] | nearly complete[2] |
| Buffer without Arg (pH, 9.5) | 7.79 | no rhGDF-5 found[1] | no rhGDF-5 found[1] | nearly complete[2] |
| Buffer A6 with 100 mM Arg (pH 9.3) | 10.03 | 3.31 | 33% | hardly any |
| Buffer A5 with 200 mM Arg (pH 8.3) | 7.62 | 1.64 | 22% | about 50%[2] |
| Buffer A9 with 300 mM Arg (pH 8.3) | 7.59 | 3.34 | 44% | little degradation[2] |
| Buffer A10 with 400 mM Arg (pH 8.3) | 7.29 | 3.57 | 49% | hardly any[2] |
| Buffer A7 with 500 mM Arg (pH 9.5) | 11.12 | 5.17 | 47% | hardly any[2] |
| Buffer A8 with 500 mM Arg (pH 8.3) | 7.68 | 4.76 | 62% | hardly any[2] |

[1] values out of calibration
[2] Grade of degradation visually judged by SDS-PAGE According to the quantitative evaluation, the grade of degradation clearly decreased with increasing arginine concentrations in the solubilization buffers (table above and FIGS. 7 and 8). However, there is still some degradation of rhGDF-5 using 400 mM arginine (dissolution buffer) A10. Hardly any (degraded) rhGDF-5 could be found in the inclusion body pellets, judged visually by SDS-PAGE and by quantitative evaluation. Thus, the solubility of rhGDF-5 in the arginine-containing solubilization buffers is good. The rhGDF-5 ratio increased with higher L-arginine concentrations in the solubilization buffers. The best rhGDF-5 ratio of 62% could be reached using arginine-containing dissolution buffer A8 (500 mM L-arginine). A concentration of at least 500 mM L-arginine in the inclusion body solubilization buffer is considered optimal for the production of rhGDF-5 and related proteins.

Example 4

Effect of L-Arginine on Ion Exchange Chromatography

The target of this experiment was to check whether a modified inclusion body solubilization buffer comprising L-arginine affects subsequent protein purification via ion exchange chromatography.

Different samples of inclusion bodies from a fermentation after solubilization were applied onto a cation exchange (CEX) column filled with column media SP Sepharose FF packed in a XK 16/20 column (CV=28 mL). Tested buffers comprised (amongst the other described components) 8M urea, no L-arginine (standard solubilization buffer) or 6M Urea, 500 mM L-arginine. (modified solubilization buffer).

Inclusion bodies were produced by disruption of GDF-5 producing *E. coli* cells with a high pressure homogenizer (three cycles, 850 bar) followed by two washes. 10.37 g of the produced IBs were solved in 100 mL modified solubilization buffer (6 M Urea buffer containing 0.5 M Arginine). 80 mL of the IB solution were left after the centrifugation, dead end filtration and sterile filtration of the IBs. 40 mL filtrated IB solution was loaded undiluted on the CEX column (approximately 172.4 mg total protein). The total protein and the rhGDF-5 content of the flow through (DL), wash and fractions of both CEX runs were analyzed.

Results: Due to an altered conductivity of the modified solubilization buffer (18 mS/cm instead of 5 mS/cm of the standard solubilization buffer), the binding to the CEX column with the modified buffer is not complete. With the modified solubilization buffer only a reduced binding to the CEX column (protein yield of 10% instead of about 60%) is possible. Therefore an additional buffer exchange step (diafiltration, e.g. through a 5 kDa cellulose membrane) prior to CEX is necessary.

Example 5

Alkaline Phosphatase (ALP) Testing of Biological Activity

The biological activity of GDF-5-related proteins and colloidal formulations thereof can be easily determined with the help of established test systems. Most useful and preferred is the common alkaline phosphatase (ALP) assay (Takuwa et al. 1989, Am. J. Physiol. 257, E797-E803). In this in vitro test system, the biological activity of GDF-5 related growth factors is measured after co-culture of different protein concentrations with osteogenic/chondrogenic cells. GDF-5 and related proteins with osteo/chondrogenic potential increase the alkaline phosphatase (ALP) expression in these cells, e.g. ATDC-5, ROB-C26 or MCHT-1/26 cells. The ALP activity in these cell lysates is determined by a colorimetric assay. The reaction is based on the hydrolysis of p-Nitrophenylphosphate (PNPP) to p-Nitrophenole, which becomes visible under alkaline conditions as the yellow p-Nitrophenolanion. The aim was to measure the activity of the tested LMP formulations by comparison of the ALP activity obtained with known concentrations of GDF-5 reference standard.

In a standardized ALP assay, $1 \times 10^4$ cells of ATDC-5 of MCHT1/26 cells were incubated overnight in 96-well plates in cell culture medium (alpha-MEM, Penicilline/Streptomycine, 2 mM L-glutamine, 10% FCS) at 37° C., 5% $CO_2$, $H_2O$-saturated. The next day, cells were stimulated with the GDF-5-related proteins or formulations thereof for 72 hrs with indicated ligand concentrations. The cells were subsequently washed with PBS (phosphate buffered saline). Cell lysis was performed in 100 µl alkaline lysis buffer 1 (0.1M glycine, pH 9.6, 1% NP-40, 1 mM $MgCl_2$, 1 mM $ZnCl_2$) for 1 h at room temperature. Then 100 µl alkaline lysis buffer 2 was added (0.1M glycine, pH 9.6, 1 mM MgCl$_2$, 1 mM ZnCl$_2$+2 mg/ml PNPP). The plates were incubated at 37° C., 5% CO$_2$, H$_2$O-saturated. The ALP-reaction was stopped afterwards with 100 µl of 30 g/l NaOH and finally the optical density was measured with an automatic microplate reader at 405 nm under consideration of blank value subtraction.

The invention claimed is:

1. A process for the production of a purified recombinant GDF-5 related protein comprising disrupting bacterial cells expressing the GDF-5 related protein in inclusion bodies with a high pressure homogenizer at a disruption pressure between 800 and 900 bar and recovering the inclusion bodies, wherein the GDF-5 related protein comprises an amino acid sequence at least 75% identical to the 102 amino acid cysteine-knot domain of GDF-5, and wherein the GDF-5 related protein increases alkaline phosphatase expression.

2. The process according to claim 1, further comprising treating the recovered inclusion bodies with a denaturing solubilization buffer comprising L-arginine.

3. The process according to claim 2 wherein the solubilization buffer contains 4-8 M urea and 400-500 mM arginine.

4. The process according to claim 3, wherein the solubilization buffer contains 6 M urea and 500 mM arginine.

5. The process according to claim 2 wherein the solubilization buffer contains a chelator in a concentration of between 5 and 100 mM.

6. The process according to claim 2 wherein the solubilization buffer has a pH between 9.0 and 11.0.

7. The process according to claim 2, further comprising removing high molecular weight contaminants directly after the inclusion body solubilization step by applying one or more means selected from the group consisting of centrifugation, depth filtration and sterile filtration.

8. The process according to claim 2, further comprising removing said L-arginine from the solution comprising solubilized inclusion body protein via diafiltration.

9. The process according to claim 2 wherein the host strain expressing the GDF-5 related protein in inclusion bodies is an *E. coli* strain.

10. The process according to claim 9, wherein the host strain expressing the GDF-5 related protein in inclusion bodies is selected from the group consisting of *E. coli* D1210 and *E. coli* W3110.

* * * * *